United States Patent [19]
Litwin et al.

[11] Patent Number: 5,770,387
[45] Date of Patent: Jun. 23, 1998

[54] ANTIBODIES TO MAMMALIAN NK ANTIGENS AND USES

[75] Inventors: Virginia M. Litwin, Palo Alto; Jennifer E. Gumperz, Oakland; Peter R. Parham, Stanford; Joseph H. Phillips, Jr., San Carlos; Lewis L. Lanier, Los Altos, all of Calif.

[73] Assignees: Schering Corporation, Kenilworth, N.J.; The Board of Trustees of The Leland Stanford Junior University, Palo Alto, Calif.

[21] Appl. No.: 670,987

[22] Filed: Jun. 28, 1996

Related U.S. Application Data

[63] Continuation of Ser. No. 188,278, Jan. 28, 1994, abandoned.
[51] Int. Cl.[6] .................... C07K 16/28; G01N 33/577
[52] U.S. Cl. .................... 435/7.24; 435/975; 530/388.3; 530/388.73; 530/389.6; 530/391.1; 530/391.3; 530/391.6
[58] Field of Search .................... 435/7.24, 975; 530/388.73, 389.6, 391.1, 391.3, 391.6, 388.3

[56] References Cited

U.S. PATENT DOCUMENTS 5,028,424  7/1991  Evans .................... 530/388.73

OTHER PUBLICATIONS

Virginia Litwin, et al., "NKB1: A Natural Killer Cell Receptor Involved in the Recognition of Polymorphic HLA–B Molecules," J. Exp. Med., 180:537–543, Aug. 1994.

Joseph H. Phillips, et al. "Superantigen–Dependent, Cell–Mediated Cytotoxicity Inhibited by MHC Class I Receptors on T Lymphocytes," Science 268:403–405, Apr. 1995.

Marco Colonna, et al. "Cloning of Immunoglobulin–Superfamily Members Associated with HLA–C and HLA–B Recognition by Human Natural Killer Cells," Science 268:405–408, Apr. 1995.

Marco Colonna, et al., "HLA–C is the inhibitory ligand that determines dominant resistance to lysis by NK1–and NK2–specific natural killer cells," Proc. Nat'l Acad. Sci., 90:12000–12004, Dec. 1993.

Marco Colonna, et al., "Generation of Allospecific Natural Killer Cells by Stimulation Across a Polymorphism of HLA–C," Science, 260:1121–1124, May 21, 1993.

Marco Colonna, et al., "Alloantigen recognition by two human natural killer cell clones is associated with HLA–C or a closely linked gene," Proc. Nat'l. Acad. Sci., 89:7983–7985, Sep. 1992.

Franz M. Karlhofer, et al., "MHC class I alloantigen specificity of Ly–49+IL–2–activated natural killer cells," Nature, 358:66–70, Jul. 2, 1992.

Ermanno Ciccone, et al., "Involvement of HLA Class I Alleles in Natural Killer (NK) Cell–specific Functions: Expression of HLA–Cw3 Confers Selective Protection from Lysis by Alloreactive NK Clones Displaying a Defined Specificty (Specificty 2)," J. Exp. Med., 176:963–971, Oct. 1992.

Paul A. Edwards, et al., "A human–human hybridoma system based on a fast–growing mutant of the ARH–77 plasma cell leukemia–derived line," Eur. J. Immunol., 12:641–648, 1982.

Klas Kärre, et al., "Selective rejection of H–2–deficient lymphoma variants suggests alternative immune defence strategy," Nature, 319:675–678, Feb. 1986.

Lewis L. Lanier, et al., "Multicolor Immunoflourescence and Flow Cytometry," Methods: A Companion to Methods in Enzymology, 2:192–199, 1991.

Lewis L. Lanier, et al., "Subpopulations of Human Natural Killer Cells Defined by Expression of the Leu–7 (HNK–1) and Leu–11 (NK–15) Antigens," J. Immunol., 131:1789–1796, Oct. 1983.

Virginia Litwin, et al., "Specificity of HLA Class I Antigen Recognition by Human NK Clones: Evidence for Clonal Heterogeneity, Protection by self and Non–self Alleles, and Influence of the Target Cell Type," J. Exp. Med., 178:1321–1336, Oct. 1993.

Hans–Gustaf Ljunggren, et al., "In search of the 'missing self': MHC molecules and NK cell recognition," Immunol. Today, 11:237–244, 1990.

Hans–Gustaf Ljunggren, et al., "Host Resistance Directed Selectively Against H–2–Deficient Lymphoma Variants: Analysis of the Mechanism," J. Exp. Med., 162:1745–1759, Dec. 1985.

Porunelloor A. Mathew, et al., "Cloning and Characterization of the 2B4 Gene Encoding a Molecule Associated with Non–MHC–Restricted Killing Mediated by Activated Natural Killer Cells and T Cells," J. Immunol., 151:5328–5337, Nov. 15, 1993.

Alessandro Moretta, et al.,"P58 Molecules as Putative Recetors for Major Histocompatability Complex (MHC) Class I Molecules in Human Natural Killer (NK) Cells. Anti–p58 Antibodies Reconstitute Lysis of MHC Class I–protected Cells in NK Clones Displaying Different Specificities," J. Exp. Med. 178:597–604, Aug. 1993.

Alessandro Moretta, et al., "Identification of Four Subsets of Human CD3⁻CD16⁺Natural Killer (NK) Cells by the Expression of Clonally Distributed Functional Surface Molecules: Correlation between Subset Assignment of NK Clones and Ability to Mediate Specific Alloantigen Recognition," J. Exp. Med., 172:1589–1598, Dec. 1990.

(List continued on next page.)

Primary Examiner—David Saunders
Attorney, Agent, or Firm—Edwin P. Ching; Sheela Mohan-Peterson

[57] ABSTRACT

Antibodies which specifically bind to an NK cell surface antigen from a mammal, reagents related thereto, including purified proteins, specific antibodies, and nucleic acids encoding said antigen. Methods of using said reagents and diagnostic kits are also provided.

28 Claims, 7 Drawing Sheets

OTHER PUBLICATIONS

Bice Perussia, et al., "Human Natural Killer Cells Analyzed by B73.1, A Monoclonal Antibody Blocking Fc Receptor Functions," *J. Immunol.*, 130:2142–2148, May 1983.

Gerald E. Piontek. et al. "YAC–1 MHC Class I Variants Reveal an Association between Decreased NK Sensitivity and Increased H–2 Expression after Interferon Treatment of in vivo Passage," *J. Immunol.*, 135:4281–4288, Dec. 1985.

Charles L. Sentman, et al., "Identification of a Subset of Murine Natural Killer Cells That Mediates Rejection of Hh–$1^d$ But Not Hh–$1^b$ Bone Marrow Grafts," *J. Exp. Med.*, 170:191–202, Jul. 1989.

Yoji Shimizu, et al., "Production of Human Cells Expressing Individual Transferred HLA–A,–B, –C Genes Using an HLA–A,–B,–C Null Human Cell Line," *J. Immunol.*, 142:3320–3328, May 1, 1989.

Yoji Shimizu, et al., "Demonstration by Class I gene transfer that reduced susceptibility of human cells to natural killer cell–mediated lysis is inversely correlated with HLA class I antigen expression," *Eur. J. Immunol.*, 19:447–451, 1989.

Walter J. Storkus, et al., "Reversal of natural killing susceptibility in target cells expressing transfected class I HLA genes," *Proc. Nat'l Acad. sci.*, 86:2361–2364, Apr. 1989.

Giorgio Trinchieri, "Biology of Narural Killier Cells," *Advances in Immunology*, 47:187–376, 1989.

Simon Wong, et al., "Ly–49 Multigene Family: New Members of a Superfamily of Type II Membrane Proteins with Lectin–Like Domains," *J. Immunol.*, 147:1417–1423, Aug. 15, 1991.

Wayne M. Yokoyama, et al., "Chromosomal Location of the Ly–49 (A1, YE1/48) Multigene Family: Genetic Association with the NK 1.1 Antigen," *J. Immunol.*, 145:2353–2358, Oct. 1, 1990.

Hans Yssel, et al., "Serum–Free Medium for Generation and Propagation of Functional Human Cytotoxic and Helper T Cell Clones," *J. Immuno. Meth.*, 72:219–227, 1984.

Jacqueline Zemmour, "The HLA–A,B 'Negative' Mutant Cell Line C1R Expresses a Novel HLA–B35 Allele Which Also Has a Point Mutation in the Translation Initiation Codon," *J. Immunol.*, 148:1941–1948, Mar. 15, 1992.

A. Moretta et al, *Jour. Exper. Medicine*, 171, 695–714, 1990.

A. N. Barclay et al, *The Leukocyte Antigen Facts Book*, Academic Press, 1993. pp. 390–391.

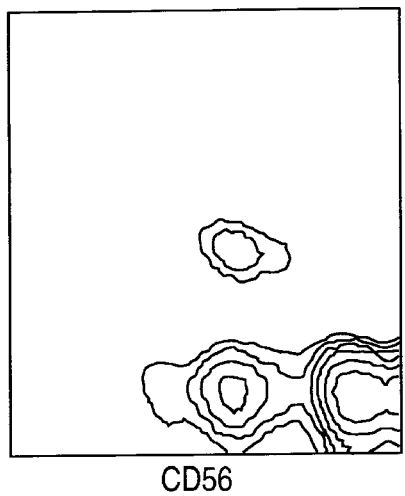
FIG. 1A
FIG. 1B
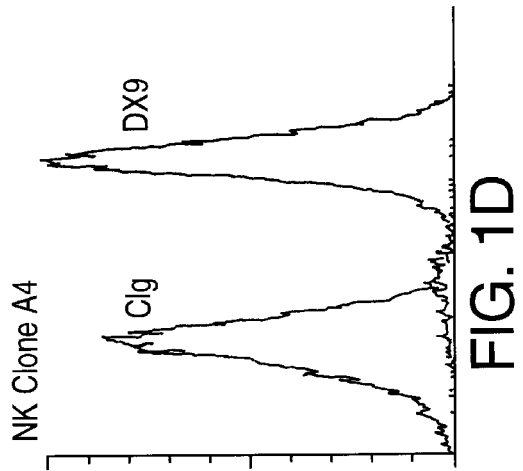
FIG. 1D
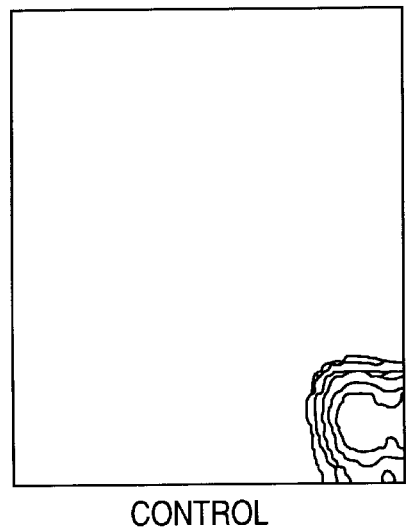
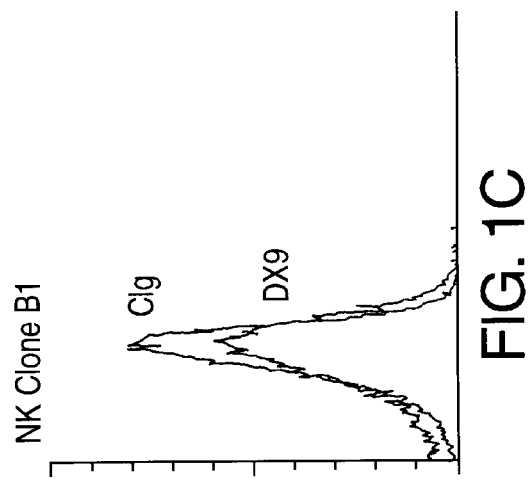
FIG. 1C

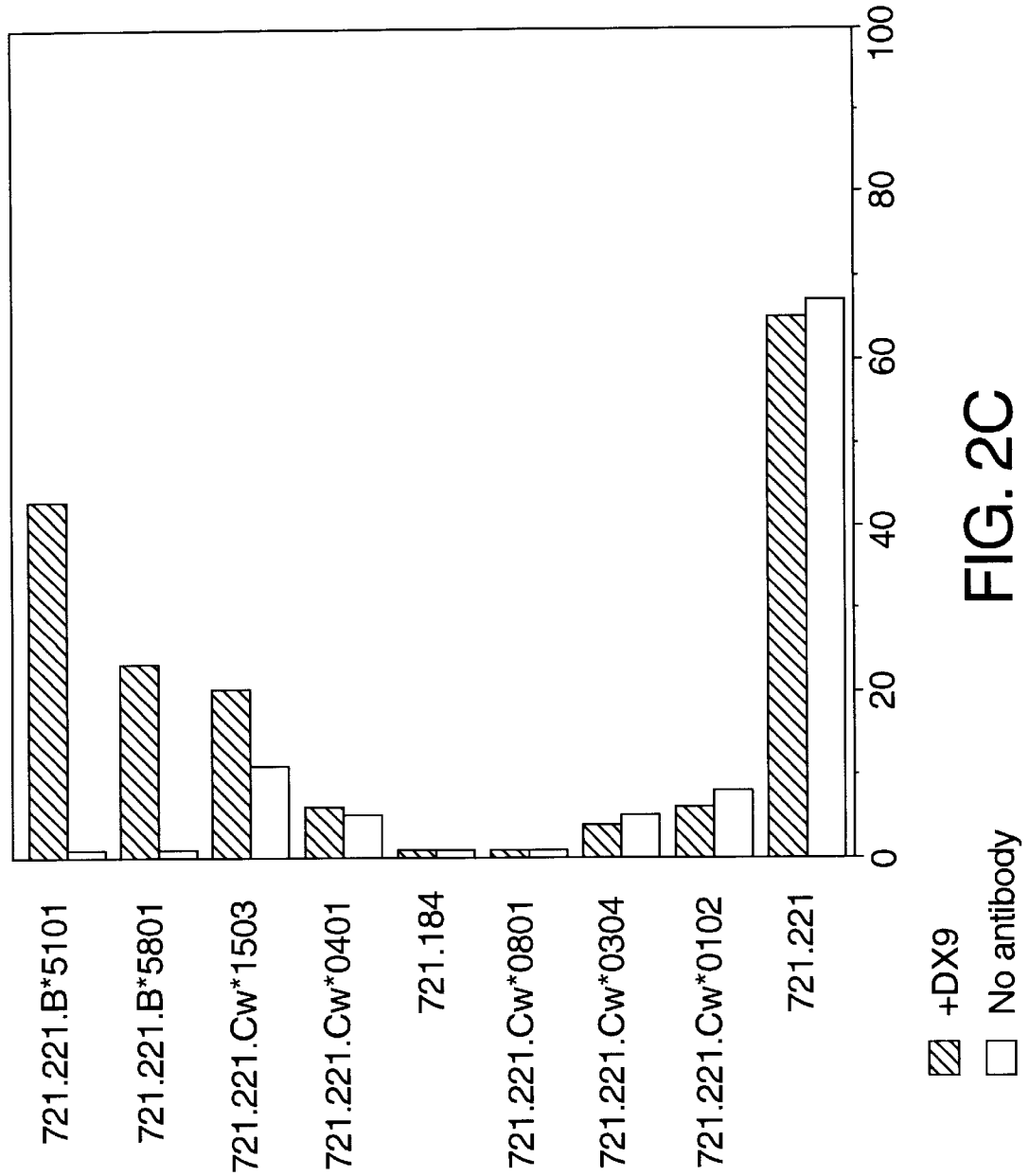

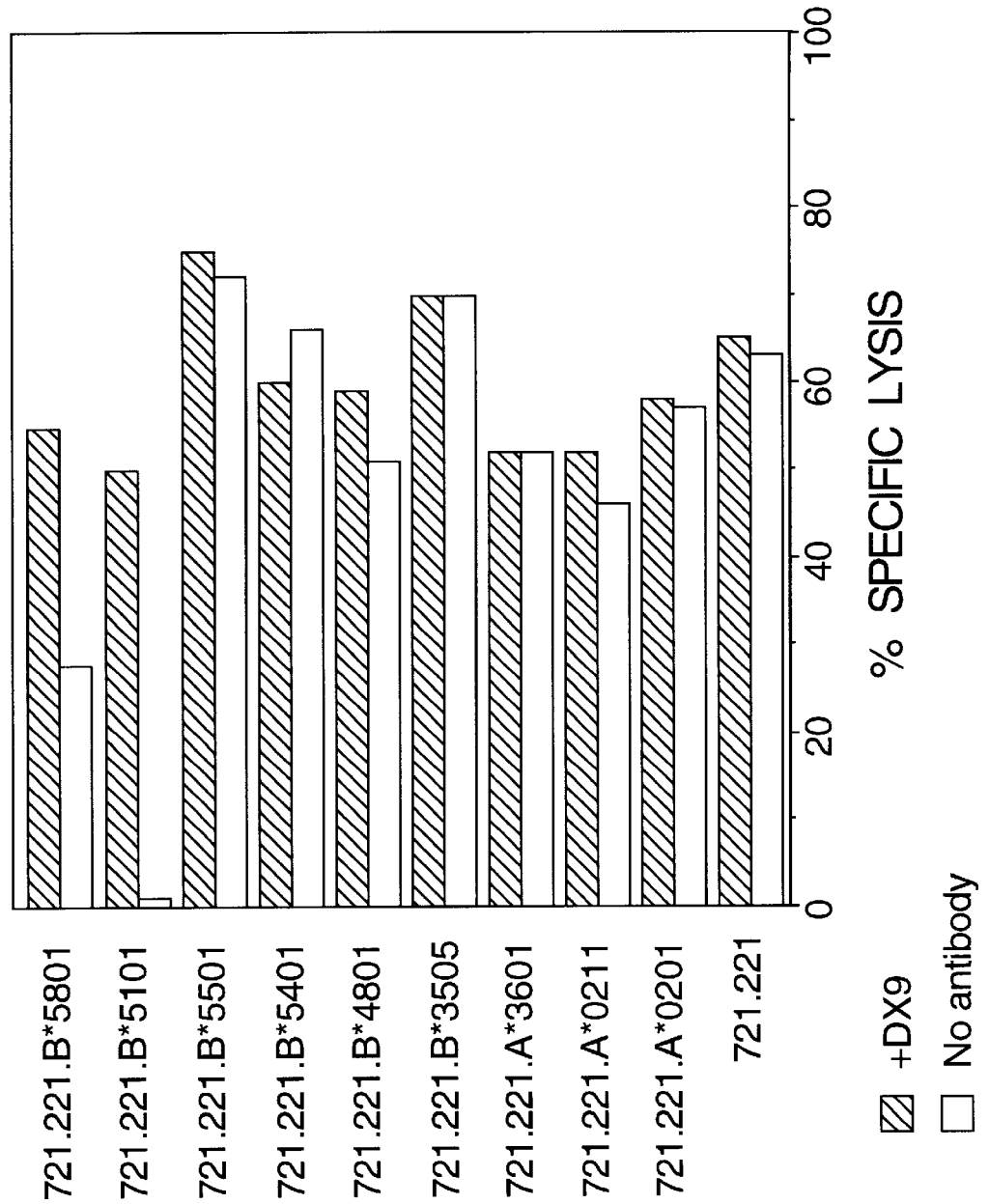

ANTIBODIES TO MAMMALIAN NK ANTIGENS AND USES

This application is a continuation of application Ser. No. 08/188,278, filed Jan. 28, 1994 and now abandoned.

FIELD OF THE INVENTION

The present invention relates to compositions which function in controlling physiology, development, and differentiation of mammalian cells, e.g., cells of a mammalian immune system. In particular, it provides antibodies, e.g., agonists and antagonists, which regulate cellular physiology, development, differentiation, or function of various cell types, including hematopoietic cells, and particularly natural killer (NK) and T cells.

BACKGROUND OF THE INVENTION

The immune system of vertebrates consists of a number of organs and several different cell types. Two major cell types include the myeloid and lymphoid lineages. Among the lymphoid cell lineage are B cells, which were originally characterized as differentiating in fetal liver or adult bone marrow, T cells, which were originally characterized as differentiating in the thymus, and natural killer (NK) cells. See, e.g., Paul (ed.) (1993) *Fundamental Immunology* (3d ed.) Raven Press, New York.

NK cells are lymphocytes distinct from T and B cells that mediate cell-mediated cytotoxicity and secrete cytokines after immune stimulation, but do not rearrange immunoglobulin (Ig) or T cell receptor (TcR) genes. See, e.g., Moretta, et al. (1994) *Adv. Immunol.* 55:341–380; and Trinchieri (1989) *Adv. Immunol.* 47:187–376.

It is becoming increasingly clear that both triggering and inhibitory molecules are involved in NK cell recognition and activation, e.g., dictating their lytic specificity. On one hand, NK cell effector function involves a positive signal that initiates cytotoxicity and cytokine production. In the case of antibody-dependent cellular cytotoxicity, the positive signal is generated by the interaction between an Ig-coated target and CD16 (FcγRIII) on the NK cell. Lanier, et al. (1983) *J. Immunol.* 131:1789–1796. However, the membrane receptors responsible for initiating lysis of transformed or virus-infected cells in the absence of specific Ig have not yet been identified.

On the other hand, NK cell-mediated cytotoxicity is also regulated by inhibitory signals. Karre and colleagues initially observed that certain murine tumor variants lacking H-2 antigens were more susceptible to NK lysis; whereas, high levels of H-2 expression correlated with resistance. Karre, et al. (1986) *Nature* 319:675–678; Ljunggren, et al. (1985) *J. Ex, Med.* 162:1745–1759. Similarly, when MHC class I molecules were transfected into human HLA-deficient B lymphoblastoid cell lines (B-LCLs), the transfectants were less susceptible to NK cell lysis than the parental lines. Storkus, et al. (1989) *Proc. Natl. Acad, Sci. USA* 86:2361–2364; Shimizu, et al. (1989) *Eur. J. Immunol.* 19:447–451. Analysis of an extensive panel of NK cell clones revealed that human NK cells have the ability to recognize multiple HLA-A, -B and -C alleles. Litwin, et al. (1993) *J. Exp. Med.* 178:1321–1336.

Karre has proposed two models which could account for this phenomenon: 1) target interference and 2) effector inhibition. The target interference model postulates that target cell MHC class I molecules mask antigens which could stimulate NK lysis. The effector inhibition model proposes that target cell MHC class I molecules may interact with specific receptors on NK cells, transmit a negative signal and prevent the initiation of cytolytic activity. Recent findings support the latter model.

Yokoyama and colleagues have identified a receptor, Ly-49, that is expressed on a subset of murine NK cells. Karlhofer, et al. (1992) *Nature* 358:66–70. The interaction between Ly-49 and H-2D$^d$ molecules on target cells prevents NK cell-mediated cytotoxicity. Genetic and biochemical characterization of Ly-49 has revealed at least 5 genes located on murine chromosome 6 which code for type II membrane glycoproteins of the C-type lectin superfamily. A member of the Ly-49 family, SW5E6, appears to be involved in hybrid resistance by mediating the rejection of Hh-incompatible expressing bone marrow cells. SW5E6 and Ly-49 are expressed as disulfide-linked homodimers; as yet, there is no evidence for heterodimers between members of the Ly-49 family. In man, NK cell receptors for HLA have not as yet been fully characterized, although Moretta and colleagues have described two antigens expressed on NK subsets that appear to correlate with recognition of HLA-C. Colonna, et al. (1992) *Proc. Natl. Acad. Sci, USA* 89:7983–7985; Ciccone, et al. (1992) *J. Exp. Med.* 176:963–971. Functional studies have demonstrated that NK clones recognize not only HLA-C, but also certain alleles of HLA-A and HLA-B, suggesting the existence of additional receptors.

However, NK cell receptors which are responsible for recognition of HLA have not been identified or characterized. Thus, a need exists to better understand the molecules involved in NK recognition and activation processes, and mechanisms of their action and interaction. The present invention provides useful reagents and methods to use them.

SUMMARY OF THE INVENTION

The present invention is based, in part, upon the discovery of an antibody which defines and recognizes a novel cell antigen found on natural killer (NK) and T cells. This monoclonal antibody is designated DX9 and the antigen it recognizes has been designated NKB1. The invention embraces These antibodies and methods for their use. In addition, it is directed to antigens recognized by these antibodies, along with variants of these proteins, e.g., mutations (muteins) of the natural sequence, species and allelic variants, fusion proteins, chemical mimetics, and other structural or functional analogs. Various uses of these different antibodies and protein compositions are also provided.

The present invention provides antibodies which bind specifically to a mammalian NKB1. In preferred embodiments the mammal is a primate; or the antibodies are a monoclonal antibody, interfere with binding of DX9 to the NKB1, or are labeled, including a fluorescent label.

The invention also provides methods of detecting a mammalian NKB1, comprising binding these antibodies to NKB1. In various embodiments, the antibody is a labeled antibody or is immobilized to a solid substrate; the NKB1 is expressed on a cell surface; the detecting allows isolation of a cell which comprises a nucleic acid which expresses NKB1; or the detecting further allows purification of NKB1. The invention also embraces a kit for detecting NKB1 with a compartment containing an antibody. In preferred embodiments, the kit is a fluorescence immunoassay kit.

The present invention further provides methods of modulating an immune function modulated by a cell comprising contacting said cell with an antibody described herein. For instance, the modulation can be blocking NK cell activation or be specific for HLA-B mediated functions.

Also embraced herein are methods for analyzing an NK cell population, comprising measuring the presence of NKB1. Typically, the measuring is a quantitative determination, e.g., by measuring binding of an antibody to NKB1.

The invention also provides substantially pure mammalian NKB1 antigens. For example, the NKB1 can be purified by immunoaffinity, e.g., using an antibody which binds specifically to a mammalian NKB1. A preferred antibody for such is DX9. Along with full length NKB1, the invention provides fragments which express an immunological epitope of said NKB1 or modulate an immune response, e.g., a response mediated by an NK cell, including an NKB1+ cell.

BRIEF DESCRIPTION OF THE FIGURES

FIGS. 1A–1D show expression of NKB1 on adult peripheral blood NK cells and NK cell clones. FIGS. 1A and 1B: Adult peripheral blood mononuclear cells were stained with fluorescein isothiocyanate (FITC)-conjugated anti-CD56 and phycoerythrin (PE) conjugated DX9 mAb or fluorochrome-conjugated control Ig. Samples were analyzed by flow cytometry. Data are displayed as contour plots (4 decade log scale). FIGS. 1C and 1D: NKB1+ and NKB1− NK cell clones were established by single cell cloning using flow cytometry. Representative NKB1− and NKB1+ NK clones were stained with phycoerythrin (PE)-DX9 monoclonal antibodies (mAb) or PE-Ig. Histograms of DX9 mab-stained cells are superimposed over histograms of Ig control-stained cells (nearest the ordinate).

FIGS. 2A–2D show the effect of DX9 mAb on the ability of NK clones to lyse HLA-deficient or HLA-transfected B-LCL target cells. Two representative NKB1$_+$ NK clones A7 (FIGS. 2A and 2B) and A4 (FIGS. 2C and 2D) were assayed for cytotoxicity against 721.221, C1R, or the indicated HLA transfectants in the presence or absence of DX9 mAb (5 µg/ml).

FIG. 3A: Viable NKB1+ NK clones were $^{125}$I labeled and lysed in 1% NP-40. Lysates were immunoprecipitated with control Ig or DX9 mAb and samples analyzed by SDS-PAGE in the presence or absence of 2-mercaptoethanol. FIG. 3B shows $^{125}$I NKB1 antigen treated with neuraminidase, O-glycanase, endo H, or N-glycanase, as indicated, and analyzed by SDS-PAGE in the presence of 2-mercaptoethanol. FIG. 3C shows viable NKB1+ NK clones metabolically labeled with $^{32}$p orthophosphate and then stimulated or not with 1 ng/ml PMA for 5 min. Cells were lysed in 1% NP-40, lysates were immunoprecipitated with control Ig, anti-HLA-A, -B, -C mAb (positive control) or DX9 mAb and samples analyzed by SDS-PAGE in the presence of 2-mercaptoethanol.

DETAILED DESCRIPTION OF THE PREFERRED EMBODIMENTS

OUTLINE

Figure 2A:
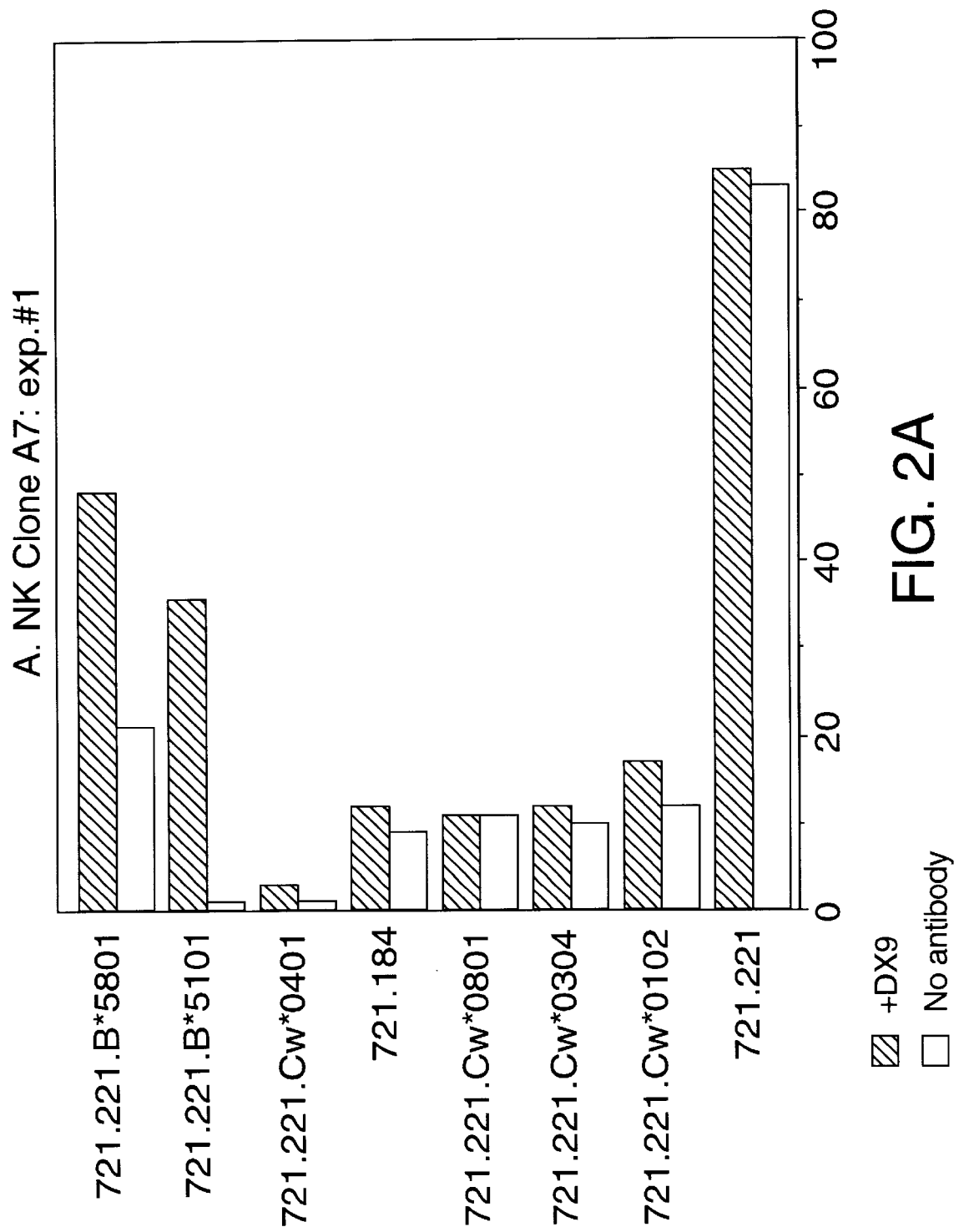
Figure 2B:
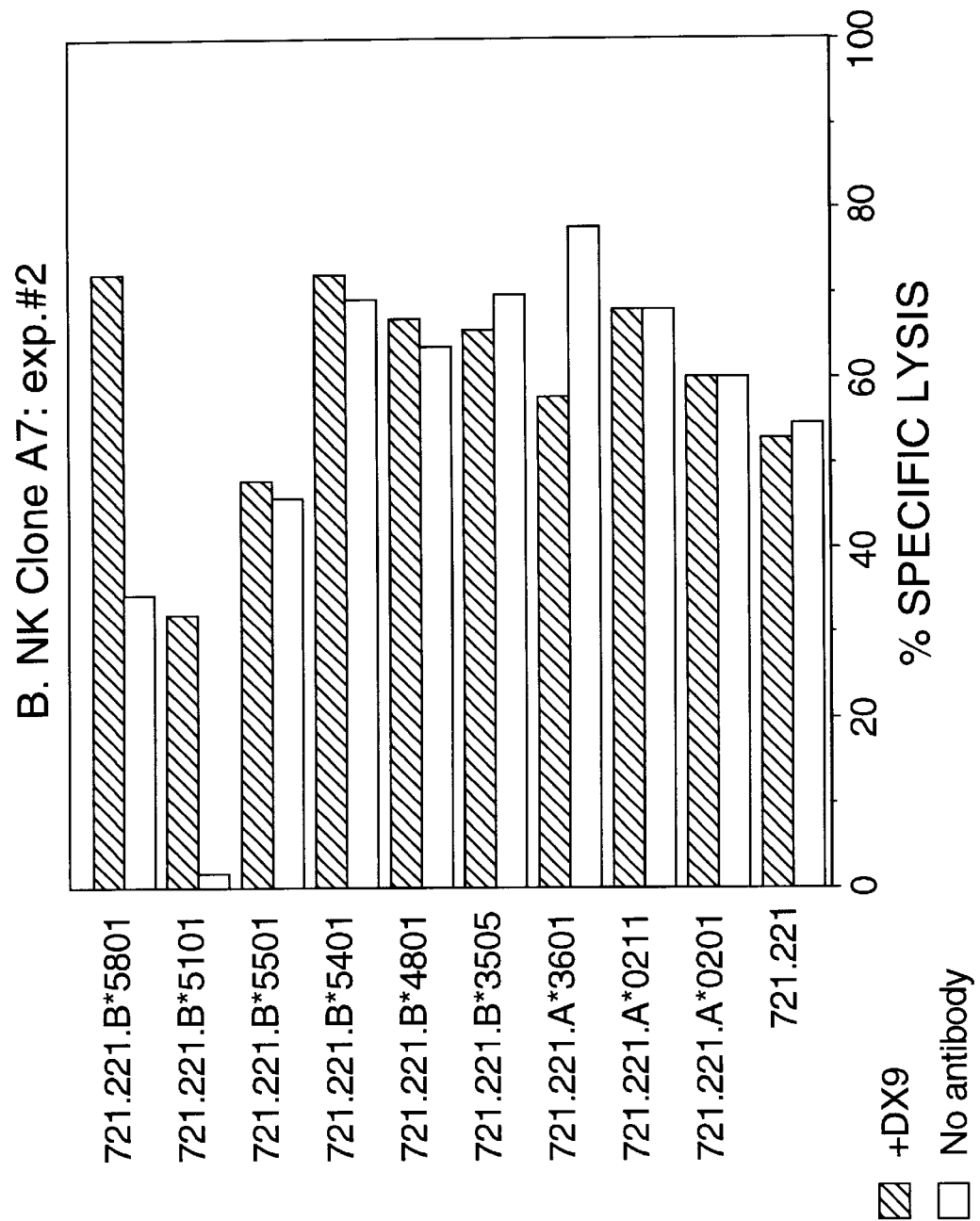

I. General
II. Antibodies
   A. polyclonal
   B. monoclonal
   C. fragments, binding compositions
III. Purified NKB1 protein
   A. physical properties
   B. biological properties
IV. Physical Variants
   A. sequence variants, fragments
   B. post-translational variants
      1. glycosylation
      2. others
V. Functional Variants
   A. analogs; fragments
      1. agonists
      2. antagonists
   B. mimetics
      1. protein
      2. chemicals
   C. species variants
VI. Nucleic Acids
   A. natural isolates; methods
   B. synthetic genes
   C. methods to isolate
VII. Making NKB1 protein; Mimetics
   A. recombinant methods
   B. synthetic methods
   C. natural purification
VIII. Uses
   A. diagnostic
   B. therapeutic
IX. Kits
   A. nucleic acid reagents
   B. protein reagents
   C. antibody reagents
X. Methods for Isolating NKB1 Specific Binding Partners
I. General The present invention provides antibodies which recognize mammalian proteins which exhibit properties characteristic of functionally significant NK and T cell expressed molecules.

These antibodies are exemplified in one embodiment by a monoclonal antibody designated DX9.

The mammalian proteins defined by the antibodies are designated NKB1 proteins. The natural proteins should be capable of mediating various physiological responses which would lead to biological or physiological responses in target cells. In particular, NK cells are responsible for immunological rejection of transplanted tissue, e.g., bone marrow transplants. The DX9 antibodies modulate various immunological responses which will affect rejection reactions.

Besides the biological activities mediated by NKB1, Table 1 discloses physical characteristics which allow distinguishing the protein from others.

Table 1: Properties of NKB1 markers.
   binds with specificity to DX9 monoclonal antibody core protein ~50 kD
   glycosylated form of protein ~70 kD, both reduced or non-reduced
   natural form of protein contains sialic acid residues
   natural form of protein contains complex N-linked oligosaccharides
   natural form typically phosphorylated
   expressed on subset of NK cells
   expressed on subset of T cells
II. Antibodies
   Antibodies can be raised to the various NKB1 proteins, including species or allelic variants, and fragments thereof. Additionally, antibodies can be raised to NKB1 proteins in either their active forms or in their inactive forms. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective NKB1 proteins, or screened for agonistic or antagonistic activity, e.g., mediated through a binding partner or counter-receptor. These monoclonal antibodies will usually bind with at least a KD of about 1 mM, more usually at least about 300 $\mu$M, typically at least about 10 $\mu$M, more typically at least about 30 $\mu$M, preferably at least about 10 $\mu$M, and more preferably at least about 3 $\mu$m or better.

The antibodies, including antigen binding fragments, of this invention can have significant diagnostic or therapeutic value. They can be potent antagonists that bind to NKB1 and inhibit binding partner interaction or inhibit the ability of the interaction to mediate a biological response. They also can be useful as non-neutralizing antibodies and can be coupled to toxins or radionuclides so that when the antibody binds to the antigen, a cell expressing it, e.g., on its surface, is killed. Further, these antibodies can be conjugated to drugs or other therapeutic agents, either directly or indirectly by means of a linker, and may effect drug targeting.

The antibodies of this invention can also be useful in diagnostic applications. As capture or non-neutralizing antibodies, they can be screened for ability to bind to the antigens without inhibiting binding by a partner. As neutralizing antibodies, they can be useful in competitive binding assays. They will also be useful in detecting or quantifying NKB1 protein or its binding partners. They will also be useful in evaluating cell populations to determine, e.g., the physiological state of an immune system.

Antigen fragments may be joined to other materials, particularly polypeptides, as fused or covalently joined polypeptides to be used as immunogens. The antigen may be purified as described below, including immunoaffinity methods using antibodies, e.g., DX9. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; and Williams, et al. (1967) *Methods in Immunology and Immunochemistry*, Vol. 1, Academic Press, New York, each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal. antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256: 495–497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells.

The result is a hybrid cell or "hybridomal" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or, alternatively, selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567. These patents are incorporated herein by reference.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified NKB1 protein will be released. Alternatively, the antibodies may be used to quantitate and identify fractionated samples containing the antigen. Standard protein purification procedures, e.g., chromatography, will be used to enrich and purify NKB1 protein with, e.g., ELISA assays, to identify fractions where NKB1 separates. Purified protein will be useful for sequencing to determine oligonucleotide sequences useful as primers or probes.

The antibodies may also be used to screen expression libraries for particular expression products. Usually the antibodies used in such a procedure will be labeled with a moiety allowing easy detection of presence of antigen by antibody binding. This will allow isolation of a cell which expresses a nucleic acid, e.g., a vector, encoding the antigen by, e.g., fluorescence activated cell sorting (FACS) analysis, and enrichment. Alternatively, an affinity method using antibodies of this invention can be used to immobilize and separate cells expressing the NKB1, e.g., encoded on a vector.

Antibodies raised against each NKB1 protein will also be useful to raise anti-idiotypic antibodies. These will be useful in detecting or diagnosing various immunological conditions related to expression of the respective antigens.

III. Purified NKB1 protein

Human NKB1 protein can be isolated from natural sources using standard biochemical purification techniques and/or by use of the antibody to determine the presence of the antigen in particular fractionation procedures. The proteins allow both sequence determination and preparation of peptides to generate antibodies to recognize such segments, As used herein, NKB1 shall encompass, when used in a protein context, a protein which, in a natural state, exhibits the properties listed in Table 1, or a significant fragment of such a protein. It also refers to a mammalian, e.g., primate, derived polypeptide which exhibits similar biological function or interacts with NKB1 protein specific binding components. These binding components, e.g., antibodies, typically bind to an NKB1 protein with high affinity, e.g., at least about 100 nM, usually better than about 30 nM, preferably better than about 10 nM, and more preferably at better than about 3 nm. One such preferred binding component is the antibody DX9.

The purified protein or peptide fragments are useful for generating antibodies by standard methods, as described below. Synthetic peptides or purified protein can be presented to an immune system to generate a specific binding composition, e.g., monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press.

The term polypeptide, as used herein, includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. Preferably, the fragment exhibits a biological property in common with the full length NKB1, e.g., immunological activity, including sharing of an epitope.

Substantially pure, in the polypeptide context, typically means that the protein is free from other contaminating proteins, nucleic acids, and other biologicals derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in most preferred embodiments, at least 99% pure. The analysis may be weight or molar percentages, evaluated, e.g., by gel staining, spectrophotometry, or terminus labeling.

A binding composition refers to molecules that bind with specificity to NKB1 protein, e.g., in a ligand-receptor type fashion, an antibody-antigen interaction, or compounds, e.g., proteins which specifically associate with NKB1 protein, e.g., in a natural physiologically relevant protein-protein interaction, either covalent or non-covalent. The molecule may be a polymer, or chemical reagent. No implication as to whether NKB1 protein is either the ligand or the receptor of a ligand-receptor interaction is represented, other than the interaction exhibit similar specificity, e.g., specific affinity. This implies both binding affinity and binding specificity. A functional analog may be a protein with structural modifications, or may be a wholly unrelated molecule, e.g., which has a molecular shape which interacts with the appropriate binding determinants. The proteins may serve as agonists or antagonists of a receptor, see, e.g., Goodman, et al. (eds.) (1990) *Goodman & Gilman's: The Pharmacological Bases of Therapeutics* (8th ed.), Pergamon Press, Tarrytown, N.Y.

Soluble fragments of both the antibodies and NKB1 antigens are provided by the invention. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the antigen.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry*, parts 1–3, W. H. Freeman & Co., San Francisco; each of which is hereby incorporated herein by reference. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30 S, more typically less than about 15 S, usually less than about 10 S, more usually less than about 6 S, and, in particular embodiments, preferably less than about 4 S, and more preferably less than about 3 S.

IV. Physical Variants

This invention also encompasses proteins or peptides having substantial amino acid sequence homology with a natural mammalian NKB1 protein or an antibody described above. The variants include species and allelic variants. A person having ordinary skill in the art will recognize that much of the following discussion of variants will apply to variants of both the NKB1 antigen and the antibodies which recognize it.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25–100% homology (if gaps can be introduced), to 50–100% homology (if conservative substitutions are included) with the amino acid sequence of the NKB1 protein. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443–453; Sankoff, et al. (1983) Chapter One in *Time Warns, Strina Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.; each of which is incorporated herein by reference.

An isolated DNA, isolated as described below, encoding an NKB1 protein can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, or antigenic activity. These modified sequences can be used to produce mutant antigens or to enhance expression. Enhanced expression may involve gene amplification, increased transcription, increased translation, and other mechanisms. Such mutant NKB1 protein derivatives include predetermined or site-specific mutations of the respective protein or its fragments. "Mutant NKB1 protein" encompasses a polypeptide otherwise falling within the homology definition of the human NKB1 protein as set forth above, but having an amino acid sequence which differs from that of NKB1 protein as found in nature, whether by way of deletion, substitution, or insertion. In particular, "site specific mutant NKB1 protein" generally includes proteins having significant homology with a natural protein with properties described in Table 1, and/or sharing various biological activities, e.g., antigenic or immunogenic, with those sequences, and in preferred embodiments include, e.g., singly substituted natural forms of the proteins. Similar concepts apply to different NKB1 proteins, particularly those found in various mammals, e.g., primates, including human. As stated before, it is emphasized that the descriptions are generally meant to encompass all mammalian NKB1 proteins.

Although site specific mutation sites are predetermined, mutants need not be site specific. NKB1 protein mutagenesis can be conducted by making amino acid insertions or deletions. Substitutions, deletions, insertions, or any combinations may be generated to arrive at a final construct. Insertions include amino- or carboxy- terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with an NKB1 polypeptide is a continuous protein molecule having sequences fused in a typical peptide-linkage, typically made as a single translation product and exhibiting properties derived from each source peptide. A similar concept applies to heterologous nucleic acid sequences.

In addition, new constructs may be made from combining similar functional domains from other proteins. For example, antigen-binding or other segments may be "swapped" between different new fusion polypeptides or fragments. See, e.g., Cunningham, et al. (1989) *Science* 243:1330–1336; and O'Dowd, et al. (1988) *J. Biol. Chem*, 263:15985–15992, each of which is incorporated herein by reference. Thus, new chimeric polypeptides exhibiting new combinations of specificities will result from the functional linkage of biologically relevant domains and other functional domains.

The phosphoramidite method described by Beaucage and Carruthers (1981) *Tetra, Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

V. Functional Variants

The blocking of physiological response mediated by NKB1 proteins may result from the inhibition of binding of the antigen to its natural binding partner, e.g., through competitive inhibition. Thus, in vitro assays of the present invention will often use isolated protein, membranes from cells expressing a recombinant membrane associated NKB1 protein, soluble fragments comprising binding segments, or fragments attached to solid phase substrates. These assays will also allow for the diagnostic determination of the effects of either binding segment mutations and modifications, or protein mutations and modifications, e.g., analogs. In particular, the NKB1 is stably expressed on NK clones, but the antigen is lost after T cell activation (T cell clones are negative).

This invention also contemplates the use of competitive drug screening assays, e.g., where neutralizing antibodies to antigen or binding partner fragments compete with a test compound for binding to the protein. In this manner, the antibodies can be used to detect the presence of any polypeptide which shares one or more antigenic binding sites of the protein and can also be used to occupy binding sites on the protein that might otherwise interact with a binding partner.

Additionally, neutralizing antibodies against the NKB1 protein and soluble fragments of the antigen which contain a high affinity receptor binding site, can be used to inhibit antigen function in tissues, e.g., tissues experiencing abnormal or undesired physiology. For instance, DX9 antibody may stimulate activation of NK cells which may modulate undesired tissue rejection in a transplantation context. "Derivatives" of the NKB1 antigens, and of antibodies, include amino acid sequence mutants, glycosylation variants, and covalent or aggregate conjugates with other chemical moieties. Covalent derivatives can be prepared by linkage of functionalities to groups which are found in the NKB1 amino acid side chains or at the N- or C- termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal-alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the NKB1 protein or fragments thereof with other proteins or polypeptides. These derivatives can be synthesized in recombinant culture such as N- or C-terminal fusions or by the use of agents known in the art for their usefulness in crosslinking proteins through reactive side groups. Preferred antigen derivatization sites with cross-linking agents are at free amino groups, carbohydrate moieties, and cysteine residues.

Fusion polypeptides between the NKB1 proteins and other homologous or heterologous proteins are also provided. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of an antigen, e.g., a receptor-binding segment, so that the presence or location of the fused antigen may be easily determined. See, e.g., Dull, et al., U.S. Pat. No. 4,859,609, which is hereby incorporated herein by reference. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

The phosphoramidite method described by Beaucage and Carruthers (1981) *Tetra, Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1–3, Cold Spring Harbor Laboratory, which are incorporated herein by reference. Techniques for synthesis of polypeptides are described, for example, in Merrifield (1963) *J. Amer. Chem.* Soc. 85:2149–2156; Merrifield (1986) *Science* 232: 341–347; and Atherton, et al. (1989) *Solid Phase Peptide Synthesis: A Practical Approach*, IRL Press, Oxford; each of which is incorporated herein by reference.

This invention also contemplates the use of derivatives of the NKB1 proteins other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of antigens or other binding proteins. For example, an NKB1 antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-NKB1 protein antibodies or its receptor or other binding partner. The NKB1 antigens can also be labeled with a detectable group, for example radioiodinated by the chloramine T procedure, covalently bound to rare earth chelates, or conjugated to another fluorescent moiety for use in diagnostic assays. Purification of NKB1 protein may be effected by immobilized antibodies or binding partners.

A solubilized NKB1 antigen or fragment of this invention can be used as an immunogen for the production of antisera or antibodies specific for the protein or fragments thereof. The purified antigen can be used to screen monoclonal antibodies or binding fragments prepared by immunization with various forms of impure preparations containing the protein. In particular, antigen binding fragments of natural antibodies are often equivalent to the antibodies themselves. The purified NKB1 proteins can also be used as a reagent to detect any antibodies generated in response to the presence of elevated levels of the protein or cell fragments containing the antigen, both of which may be diagnostic of an abnormal or specific physiological or disease condition. Additionally, antigen fragments may also serve as immunogens to produce further antibodies of the present invention, as described immediately below. For example, this invention contemplates antibodies raised against amino acid sequences from proteins having properties described in Table 1, or fragments of them. In particular, this invention contemplates antibodies having binding affinity to or being raised against specific fragments which are predicted to lie outside of the lipid bilayer, e.g., domain structures.

The invention also provides means to isolate a group of related antigens displaying both distinctness and similarities in structure, expression, and function. Elucidation of many of the physiological effects of the antigens will be greatly accelerated by the isolation and characterization of distinct species variants. In particular, the present invention provides useful probes for identifying additional homologous genetic entities in different species.

Isolated genes will allow transformation of cells lacking expression of a corresponding NKB1 protein, e.g., either species types or cells which lack corresponding antigens and should exhibit negative background biological activity. Expression of transformed genes will allow isolation of antigenically pure cell lines, with defined or single specie variants. This approach will allow for more sensitive detection and discrimination of the physiological effects of NKB1 proteins. Subcellular fragments, e.g., cytoplasts or membrane fragments, can be isolated and used.

Dissection of the critical structural elements which effect the various physiological or differentiation functions provided by the proteins is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390; each of which is incorporated herein by reference.

In particular, functional domains or segments can be substituted between species variants or related proteins to determine what structural features are important in both binding partner affinity and specificity, as well as signal transduction. An array of different variants will be useful to screen for molecules exhibiting combined properties of interaction with different species variants of binding partners.

Antigen internalization may occur under certain circumstances, and interaction between intracellular components and "extracellular" segments of proteins involved in interactions may occur. The specific segments of interaction of NKB1 protein with other intracellular components may be identified by mutagenesis or direct biochemical means, e.g., cross-linking or affinity methods. Structural analysis by crystallographic or other physical methods will also be applicable. Further investigation of the mechanism of biological function will include study of associated components which may be isolatable by affinity methods or by genetic means, e.g., complementation analysis of mutants.

Further study of the expression and control of NKB1 protein will be pursued. The controlling elements associated with the antigens may exhibit differential developmental, tissue specific, or other expression patterns. Upstream or downstream genetic regions, e.g., control elements, are of interest.

Structural studies of the antigen will lead to design of new variants, particularly analogs exhibiting agonist or antagonist properties on binding partners. This can be combined with previously described screening methods to isolate variants exhibiting desired spectra of activities.

Expression in other cell types will often result in glycosylation differences in a particular antigen. Various species variants may exhibit distinct functions based upon structural differences other than amino acid sequence. Differential modifications may be responsible for differential function, and elucidation of the effects are now made possible.

Thus, the present invention provides important reagents related to antigen-binding partner interaction. Although the foregoing description has focused primarily upon the human NKB1 protein, those of skill in the art will immediately recognize that the invention encompasses other closely related antigens, e.g., other primate species or allelic variants, as well as variants and other members of the family.

VI. Nucleic Acids

Table 1 discloses the properties of natural NKB1 protein which allow for purification of the protein. This provides means to isolate nucleic acids encoding such proteins, and determination of the sequence provides a handle to other members of the NKB1 family. Such nucleotide sequences and related reagents are useful in constructing a DNA clone useful for expressing NKB1 protein, or, e.g., isolating a homologous gene from another natural source, including other members of the family. Typically, the sequences will be useful in isolating other genes, e.g., allelic variants or alternatively spliced isoforms, from human.

For example, a specific binding composition such as DX9 could be used for screening of an expression library made from a cell line which expresses an NKB1 protein. The screening can be standard staining of surface expressed protein, or by panning. Screening of intracellular expression can also be performed by various staining or immunofluorescence procedures. The binding compositions could be used to affinity purify or sort out cells expressing the protein.

This invention contemplates use of isolated DNA or fragments to encode a biologically active NKB1 protein or polypeptide. In addition, this invention covers isolated or recombinant DNA which encodes a biologically active protein or polypeptide and which is capable of hybridizing under appropriate conditions with the DNA sequences. Said biologically active protein or polypeptide can be a full length antigen, or fragment. Further, this invention covers the use of isolated or recombinant DNA, or fragments thereof, which encode proteins which are homologous to an NKB1 protein or which were isolated using cDNA encoding an NKB1 protein as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Alternatively, a purified species may be separated from host components from a recombinant expression system.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides.

A DNA which codes for an NKB1 protein will be particularly useful to identify genes, mRNA, and cDNA species which code for related or homologous proteins, as well as DNAs which code for homologous proteins. There should be homologues in other mammals, e.g., primates. Various NKB1 proteins should be homologous and are encompassed herein. However, even proteins that have a more distant evolutionary relationship to the antigen can readily be isolated under appropriate conditions using these sequences if they are sufficiently homologous. Primate NKB1 proteins are of particular interest.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987) (ed.) *Teratocarcinomas and Embryonic Stem Cells: A Practical Approach* IRL Press, Oxford; Rosenberg (1992) *J. Clinical Oncology* 10:180–199; and Cournoyer and Caskey (1993) *Ann. Rev. Immunol.* 11:297–329; each of which is incorporated herein by reference.

Homologous nucleic acid sequences, when compared, exhibit significant similarity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence as described. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203–213, which is incorporated herein by reference. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349–370, which is hereby incorporated herein by reference.

VII. Making NKB1 protein; Mimetics

DNA which encodes the NKB1 protein or fragments thereof can be obtained by chemical synthesis, screening cDNA libraries, or by screening genomic libraries prepared from a wide variety of cell lines or tissue samples.

This DNA can be expressed in a wide variety of host cells for the synthesis of a full-length protein or fragments which can in turn, for example, be used to generate polyclonal or monoclonal antibodies; for binding studies; for construction and expression of modified molecules; and for structure/function studies. Each antigen or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encodes an NKB1 protein, or a fragment thereof, preferably encoding a biologically active polypeptide. The DNA can be under the control of a viral promoter and can encode a selection marker. This invention further contemplates use of such expression vectors which are capable of expressing eukaryotic cDNA coding for an NKB1 protein in a prokaryotic or eukaryotic host, where the vector is compatible with the host and where the eukaryotic cDNA coding for the antigen is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the antigen or its fragments in various hosts using vectors that do not contain a replication origin that is recognized by the host cell. It is also possible to use vectors that cause integration of an NKB1 gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y.; and Rodriquez, et al. (1988) (eds.) *Vectors: A Survey of Molecular Clonina Vectors and Their Uses*, Buttersworth, Boston, Mass.; which are incorporated herein by reference.

Transformed cells include cells, preferably mammalian, that have been transformed or transfected with vectors containing an NKB1 gene, typically constructed using recombinant DNA techniques. Transformed host cells usually express the antigen or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, either from the culture or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the NKB1 proteins or its fragments include, but are not limited to, such vectors as those containing the lac promoter (pUC-series); trp promoter (pBR322-trp); lpp promoter (the pIN-series); lambda-pP or pR promoters (pOTS); or hybrid promoters such as ptac (pDR540). See Brosius, et al. (1988) "Expression Vectors Employing Lambda-, trp-, lac-, and lpp-derived Promoters", in Rodriguez and Denhardt (eds.) *Vectors*: A Survey of Molecular Clonina Vectors and Their Uses, Buttersworth, Boston, Chapter 10, pp. 205–236, which is incorporated herein by reference.

Lower eukaryotes, e.g., yeasts and Dictyostelium, may be transformed with vectors encoding NKB1 proteins. For purposes of this invention, the most common lower eukaryotic host is the baker's yeast, Saccharomyces cerevisiae. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active NKB1 protein. In principle, any higher eukaryotic tissue culture cell line is workable, e.g., insect baculovirus expression systems, whether from an invertebrate or vertebrate source. However, mammalian cells are preferred, in that the processing, both cotranslationally and posttranslationally. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985)

*Mol. Cell Biol.* 5:1136–1142; pMC1neo Poly-A, see Thomas, et al. (1987) *Cell* 51:503–512; and a baculovirus vector such as pAC 373 or pAC 610.

It will often be desired to express an NKB1 protein polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the NKB1 protein gene may be co-transformed with one or more genes encoding mammalian or other glycosylating enzymes. Using this approach, certain mammalian glycosylation patterns will be achievable or approximated in prokaryote or other cells.

The NKB1 protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Now that the NKB1 protein has been described, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York; all of each are incorporated herein by reference. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The NKB1 protein, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149–2156, which is incorporated herein by reference.

The prepared protein and fragments thereof can be isolated and purified from the reaction mixture by means of peptide separation, for example, by extraction, precipitation, electrophoresis and various forms of chromatography, and the like. The NKB1 proteins of this invention can be obtained in varying degrees of purity depending upon its desired use. Purification can be accomplished by use of the protein purification techniques disclosed herein or by the use of the antibodies herein described in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the protein, or lysates or supernatants of cells producing the NKB1 protein as a result of DNA techniques, see below.

VIII. Uses

The present invention provides reagents which will find use in diagnostic applications as described elsewhere herein, e.g., in the general description for physiological or developmental abnormalities, or below in the description of kits for diagnosis.

This invention also provides reagents with significant therapeutic value. The NKB1 protein (naturally occurring or recombinant), fragments thereof, and antibodies thereto, along with compounds identified as having binding affinity to NKB1 protein, will be useful in the treatment of conditions associated with abnormal or undesired physiology or development, including abnormal proliferation, e.g., cancerous conditions, or degenerative conditions. Abnormal or undesired proliferation, regeneration, degeneration, and atrophy may be modulated by appropriate therapeutic treatment using the compositions provided herein. For example, a disease, disorder, or undesired response associated with expression or signaling by an NKB1 antigen should be a likely target for an agonist or antagonist of the protein.

In particular, NK cell function is important in mediating transplantation rejection responses, e.g. in bone marrow and other tissue grafts. The DX9 has been shown to block activation of various NK cells. Thus, other binding compositions, e.g., antibodies, which block NKB1 signal function will be useful in modulating tissue rejection or graft v. host responses, and may also be useful in controlling such conditions as autoimmune responses.

Other abnormal developmental conditions are known in the cell types shown to possess NKB1 antigen, e.g., NK cells and certain T cells. See Berkow (ed.) *The Merck Manual of Diagnosis and Therapy* Merck & Co., Rahway, N.J.; and Thorn, et al. *Harrison's Principles of Internal Medicine* McGraw-Hill, New York. These problems may be susceptible to prevention or treatment using compositions provided herein.

Recombinant antibodies which bind to NKB1 can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Screening using NKB1 for binding partners or compounds having binding affinity to NKB1 antigen can be performed, including isolation of associated components. Subsequent biological assays can then be utilized to determine if the compound has intrinsic biological activity and is therefore an agonist or antagonist in that it blocks an activity of the antigen. This invention further contemplates the therapeutic use of antibodies to NKB1 protein as antagonists. This approach will be particularly useful with other NKB1 protein species variants and other members of the family.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics* 8th Ed., Pergamon Press, Tarrytown, N.Y.; and *Remington's Pharmaceutical Sciences* 17th ed. (1990), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index* Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

NKB1 protein, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics*, 8th Ed., Pergamon Press, Tarrytown, N.Y.; and *Remington's Pharmaceutical Sciences*, 17th ed. (1990) Mack Publishing Co., Easton, Pa.; each of which is hereby incorporated herein by reference. The therapy of this invention may be combined with or used in association with other therapeutic agents.

Both the naturally occurring and the recombinant forms of the NKB1 specific antibodies and the NKB1 proteins of this invention are particularly useful in kits and assay methods which are capable of screening compounds for binding activity. Several methods of automating assays have been developed in recent years so as to permit screening of tens of thousands of compounds in a short period. See, e.g., Fodor, et al. (1991) *Science* 251:767–773, which is incorporated herein by reference and which describes means for testing of binding affinity by a plurality of defined polymers synthesized on a solid substrate. The development of suitable assays can be greatly facilitated by the availability of large amounts of purified, soluble NKB1 protein as provided by this invention.

This invention is particularly useful for screening compounds by using recombinant antigen in any of a variety of drug screening techniques. The advantages of using a recombinant protein in screening for specific ligands include: (a) improved renewable source of the antigen from a specific source; (b) potentially greater number of antigen molecules per cell giving better signal to noise ratio in assays; and (c) species variant specificity (theoretically giving greater biological and disease specificity). The purified protein may be tested in numerous assays, typically in vitro assays, which evaluate biologically relevant responses. See, e.g., Coligan *Current Protocols in Immunology*; Hood, et al. *Immunology* Benjamin/Cummings; Paul (ed.)(1993) *Fundamental Immunology*; and *Methods in Enzymology* Academic Press. This will also be useful in screening for a ligand which binds an NKB1, e.g., from an interacting cell.

One method of drug screening utilizes eukaryotic or prokaryotic host cells which are stably transformed with recombinant DNA molecules expressing the NKB1 antigens. Cells may be isolated which express an antigen in isolation from other functionally equivalent antigens. Such cells, either in viable or fixed form, can be used for standard protein-protein binding assays. See also, Parce, et al. (1989) *Science* 246:243–247; and Owicki, et al. (1990) *Proc. Nat'l Acad. Sci. USA* 87:4007–4011; which are incorporated herein by reference and describe sensitive methods to detect cellular responses. Competitive assays are particularly useful, where the cells (source of NKB1 protein) are contacted and incubated with a labeled binding partner or antibody having known binding affinity to the ligand, such as $^{125}$I-antibody, and a test sample whose binding affinity to the binding composition is being measured. The bound and free labeled binding compositions are then separated to assess the degree of antigen binding. The amount of test compound is inversely proportional to the amount of labeled receptor binding to the known source. Numerous techniques can be used to separate bound from free antigen to assess the degree of binding. This separation step could typically involve a procedure such as adhesion to filters followed by washing, adhesion to plastic followed by washing, or centrifugation of the cell membranes. viable cells could also be used to screen for the effects of drugs on NKB1 protein mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as a source of NKB1 protein. These cells are stably transformed with DNA vectors directing the expression of a membrane associated NKB1 protein, e.g., an engineered membrane bound form. Essentially, the membranes would be prepared from the cells and used in a receptor/ligand type binding assay such as the competitive assay set forth above.

Still another approach is to use solubilized, unpurified or solubilized, purified NKB1 protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to NKB1 and is described in detail in Geysen, European Patent Application 84/03564, published on Sep. 13, 1984, which is incorporated herein by reference. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified NKB1 binding composition, and washed. The next step involves detecting bound binding composition.

Rational drug design may also be based upon structural studies of the molecular shapes of the NKB1 protein and other effectors or analogs. Effectors may be other proteins which mediate other functions in response to antigen binding, or other proteins which normally interact with the antigen, e.g., NKB1 ligand. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York, which is hereby incorporated herein by reference.

Purified NKB1 protein can be coated directly onto plates for use in the aforementioned drug screening techniques. However, non-neutralizing antibodies to these ligands can be used as capture antibodies to immobilize the respective ligand on the solid phase.

IX. Kits

This invention also contemplates use of NKB1 proteins, fragments thereof, peptides, their fusion products, and binding compositions in a variety of diagnostic kits and methods for detecting the presence of a binding composition. Typically the kit will have a compartment containing either a defined NKB1 peptide or gene segment or a reagent which recognizes one or the other, e.g., antigen fragments or antibodies. See, e.g., Chen (ed.) (1987) *Immunoassay: A Practical Guide* Academic Press, Orlando, Fla.; Price and Newman (eds.) (1991) *Principles and Practice of Immunoassay* Stockton Press, New York; and Ngo (ed.) (1988) *Nonisotopic Immunoassay* Plenum Press, NY.

A kit for determining the binding affinity of a test compound to an NKB1 protein would typically comprise a test compound; a labeled compound, for example an antibody having known binding affinity for the antigen; a source of NKB1 protein (naturally occurring or recombinant); and a means for separating bound from free labeled compound, such as a solid phase for immobilizing the antigen. Once compounds are screened, those having suitable binding affinity to the antigen can be evaluated in suitable biological assays, as are well known in the art, to determine whether they exhibit similar biological activities to the natural antigen. The availability of recombinant NEB1 protein polypeptides also provide well defined standards for calibrating such assays.

A preferred kit for determining the concentration of, for example, an NKB1 protein in a sample would typically comprise a labeled compound, e.g., antibody, having known binding affinity for the antigen, a source of antigen (naturally occurring or recombinant) and a means for separating the bound from free labeled compound, for example, a solid phase for immobilizing the NKB1 protein. Compartments containing reagents, and instructions, will normally be provided.

One method for determining the concentration of NKB1 protein in a sample would typically comprise the steps of: (1) preparing membranes from a sample comprised of a membrane bound NKB1 protein source; (2) washing the membranes and suspending them in a buffer; (3) solubilizing the antigen by incubating the membranes in a culture medium to which a suitable detergent has been added; (4) adjusting the detergent concentration of the solubilized antigen; (5) contacting and incubating said dilution with radiolabeled antibody to form complexes; (6) recovering the complexes such as by filtration through polyethyleneimine treated filters; and (7) measuring the radioactivity of the recovered complexes.

Antibodies, including antigen binding fragments, specific for the NKB1 protein or fragments are useful in diagnostic applications to detect the presence of elevated levels of NKB1 protein and/or its fragments. Such diagnostic assays can employ lysates, live cells, fixed cells, immunofluorescence, cell cultures, body fluids, and further can involve the detection of antigens related to the protein in serum, or the like. Diagnostic assays may be homogeneous (without a separation step between free reagent and protein-protein complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to an NKB1 protein or to a particular fragment thereof. Similar assays have also been extensively discussed in the literature. See, e.g., Harlow and Lane (1988) *Antibodies: A Laboratory Manual*, CSH.

Anti-idiotypic antibodies may have similar use to diagnose presence of antibodies against an NKB1 protein, as such may be diagnostic of various abnormal states. For example, overproduction of NKB1 protein may result in production of various immunological reactions which may be diagnostic of abnormal physiological states, particularly in proliferative cell conditions such as cancer or abnormal differentiation.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled NKB1 protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the antigen, test compound, NKB1 protein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free antigen, or alternatively the bound from the free test compound. The NKB1 protein can be immobilized on various matrixes followed by washing. Suitable matrixes include plastic such as an ELISA plate, filters, and beads. Methods of immobilizing the NKB1 protein to a matrix include, without limitation, direct adhesion to plastic, use of a capture antibody, chemical coupling, and biotin-avidin. The last step in this approach involves the precipitation of protein-protein complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678, each of which is incorporated herein by reference.

The methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an NKB1 protein. These sequences can be used as probes for detecting levels of antigen message in samples from patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$p. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

X. Methods for Isolating NKB1 Specific Binding Partners

The NKB1 protein should interact with a ligand based, e.g., upon its similarity in structure and function to other cell markers exhibiting developmental and cell type specificity of expression. Methods to isolate a ligand are made available by the ability to make purified NKB1 for screening programs. Soluble or other constructs using the NKB1 sequences provided herein will allow for screening or isolation of NKB1 specific ligands.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning. A Laboratory Manual* Cold Spring Harbor Laboratory, Cold Spring Harbor Press; Sambrook, et al. (1989) *Molecular Cloning: A Laboratory Manual* (2d ed.), vols 1–3, CSH Press, NY; Ausubel, et al., Biology, Greene Publishing Associates, Brooklyn, N.Y.; or Ausubel, et al. (1987 and Supplements) *Current Protocols in Molecular Biology* Greene/Wiley, New York; Innis, et al. (eds.) (1990) *PCR Protocols: A Guide to Methods and Applications* Academic Press, N.Y.; all of which are each incorporated herein by reference. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology* vol. 182, and other volumes in this series; and manufacturer's literature on use of protein purification products, e.g., Pharmacia, Piscataway, N.J., or Bio-Rad, Richmond, Calif.; which are incorporated herein by reference. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexpress: The High Level Expression & Protein Purification System* QUIAGEN, Inc., Chatsworth, Calif.: which are incorporated herein by reference.

FACS analyses are described in Melamed, et al. (1990) Flow *Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. NK clones.

Normal human peripheral blood was purchased from the Stanford Blood Bank, Stanford, Calif. NK cell clones (CD3$^-$,CD56$^+$) were established using the culture conditions described by Yssel, et al. (1984) *J. Immunol, Methods* 72:219–227.

III. mAb and flow cytometry.

Various mAb were generously provided by Becton Dickinson Immunocytometry Systems, San Jose, Calif. Cy-chrome™ conjugated anti-CD3 was purchased from Pharmingen, San Diego, Calif. DX9 (IgG1) hybridoma was generated by immunizing Balb/c mice with human NK clone VL186-1 (a clone characterized as CD3$^-$,CD16$^+$,CD56$^+$) and fusing splenocytes with Sp2/0. Fab and F(ab')2 fragments were prepared using immobilized papain or immobilized pepsin (Pierce Chemicals, Rockford, Ill.), respectively, and intact mAb was removed by protein A affinity chromatography. Methods of immunofluorescent staining and flow cytometry have been described. Lanier, et al. (1991) *Methods: A Companion to Methods in Enzymology* 2:192–199.

IV. Biochemistry.

Viable cells were labeled with $^{125}$I using lactoperoxidase/glucose oxidase or with $^{32}$P-orthophosphate (Amersham, Arlington Heights, Ill.). Lanier, et al. (1988) *J. Exp. Med.* 167:1572–1585. Cells were lysed in Tris buffered saline 50 mM Tris, 15 mM NaCl, pH 8.0) containing 1% NP-40 and protease and phosphatase inhibitors or 20 mM triethanolamine/150 mM NaCl buffer (pH 7.8) containing 1% digitonin (CalBiochem, La Jolla, Calif.) and 0.12% Triton X-100 (Sigma) with protease inhibitors. NKB1 antigen was immunoprecipitated, as described. Lanier, et al. (1988) *J. Exp. Med.* 167:1572–1585. NKB1 glycoprotein was treated with neuraminidase (Sigma), O-glycanase (Genzyme, Boston, Mass.), and N-glycosidase F (Boehringer Mannheim, Indianapolis, Ind.) according to the techniques provided by the manufacturers. Samples were analyzed by SDS-PAGE.

V. Cytotoxicity assays.

NK cell-mediated cytotoxicity was measured using a 4 hr $^{51}$Cr radioisotope release assay at an effector to target ratio of 6:1 in the presence and absence of DX9 mAb (5 µg/ml). Lanier, et al. (1983) *J. Immunol.* 131:1789–1796. C1R B-LCL (Edwards, et al. (1982) *Eur. J. Immunol.* 12:641–648; 648 and Zemmour, et al. (1992) *J. Immunol.* 148:1941–1948) (HLA-A$^-$,-B*3503$^{LOW}$,-Cw*0401+) and C1R transfectants expressing HLA-A*0201, -A*0301, -A*6801, -B*3701 and -B*5801 were generously provided by Dr. Peter Cresswell (Yale University, New Haven, Conn.) and Dr. Jeffrey Dawson (Duke University, Durham, N.C.). 721.221 (HLA-A$^-$, -B$^-$, -C$^-$) and 721.221.B*5101 and 721.221.Cw*0301 transfectants were generously provided by Dr. Robert DeMars (University of Wisconsin, Madison, Wis.). See Shimizu, et al. (1989) *J. immunol.* 142:3320–3328. 721.221 transfectants expressing HLA-A*0211, -A*3601, -B*3505,-B*4801, -B*5401, -B*5501, -B*5901, -Cw*0102, -Cw*0304, -Cw*0401, -Cw*0801, -Cw*1503 were generated as previously described. Litwin, et al. (1993) *J. Exp. Med.* 178:1321–1336.

VI. Generation and characterization of DX9 mAb.

While NK cell clones and polyclonal NK populations frequently kill MHC class I-deficient B-LCL C1R and 721.221, transfection with certain alleles of HLA-A, -B, or -C results in protection from NK cell lysis. In particular, certain alleles of HLA-B were recognized by a high frequency of NK clones. In order to identify NK cell receptors for HLA, mAb were generated against an NK clone (VL186-1, described above) which was strongly inhibited from lysing HLA-B*5801 transfected B-LCL targets. Litwin, et al. (1993) *J. Exp, Med.* 178:1321–1336. In a hybridoma screening assay, mAb were selected which were able to induce lysis of HLA-B*5801 B-LCL transfectants. NK clone VL186-1 normally does not kill the HLA-B*5801 transfected B-LCL (0% cytotoxicity). However, in the presence of mAb DX9 64% lysis of the HLA-B*5801 transfected B-LCL was observed. DX9 mAb reacted with NK clone VL186-1, but failed to stain the HLA-B*5801 transfected B-LCL, indicating that the effect was due to interaction with the NK effector cell and not the target.

Fab and F(ab')2 fragments of DX9 mAb were as efficient as intact Ig and induced lysis of the HLA-B*5801 transfected B-LCL at concentrations ranging from 0.3 µg/ml to 5 µg/ml.

The DX9 monoclonal antibody has been deposited according to the Budapest Treaty with the American Type Culture Collection (ATCC), 12301 Parklawn Drive, Rockville, Md. 20852, on Dec. 13, 1994. The deposit has been assigned accession number HB11775.

The antigen recognized by DX9 mAb, designated NKB1, is present on a subset of CD3$^-$,CD56$^+$ NK cells in adult peripheral blood (FIGS. 1A–1D), but is not expressed on granulocytes, monocytes, thymocytes, or B lymphocytes. Analysis of peripheral blood from 18 normal adult donors indicated that NKB1 is present on from <0.1% to 61% (mean=14%) of CD3$^-$,CD56$^+$ NK cells. The significance of this heterogeneity is unknown. NKB1 was infrequently observed on adult peripheral blood CD3$^+$ lymphocytes, although a minor subset (<0.1–3%) of NKB1$^+$ T cells could be detected in certain individuals. A panel of NKB1$^-$ and NKB1$^+$ NKclones (CD3$^-$,CD56$^+$) were established by single cell cloning using flow cytometry for further analysis. In all cases, the NKB1 phenotype of the clones remained stable (representative clones are shown in FIGS. 1A–1D). NK clones initially isolated as NKB1$^-$ have not been observed to acquire NKB1, nor NK clones originally isolated as NKB1$^+$ to lose NKB1.

VII. HLA specificity of NKB1.

NK clones were established from two donors on the basis of NKB1 expression (CD$^-$,CD56$^+$,NKB1$^+$ and CD$^-$,CD56$^+$,NKB1$^-$). Of 29 NKB1$^+$ NK clones examined, all lysed HLA-deficient EBV transformed B-LCL and demonstrated diminished lytic activity against HLA-B*5801 transfectants. Cytotoxicity against the HLA-B*5801 transfectant was substantially augmented in the presence of DX9 mAb with all NKB$^+$ NK cell clones (see FIGS. 2A–2D and Table 2). By contrast, killing of the untransfected HLA-deficient EBV transformed B-LCL cell lines 721.221 and C1R by NKB1$^+$ NK clones was neither augmented nor inhibited by DX9 mAb. Examination of a broad panel of HLA transfectants indicated that DX9 mAb induced cytotoxicity against certain HLA-B alleles in addition to HLA-B*5801, but did not affect cytotoxicity against any HLA-C transfectants examined. Representative data from two NKB1$^+$ clones are shown in FIGS. 2A–2D and results from several NKB1$^-$ and NKB1$^+$ NK clones are summarized in Table 2. While NKB1$^+$ NK clones recognized and failed to lyse transfectants expressing certain HLA-C alleles (including -Cw*0102, -Cw*0301, -Cw*0304, -Cw*0401, -Cw*0801, -Cw*1503) the presence of DX9 mAb had no effect on the target protection conferred by these molecules.

TABLE 2

Lysis of HLA transfected target cells in the presence and absence of DX9 mAb.

| | C1R transfectants | | | | 721.221 transfectants | | | | | | | |
|---|---|---|---|---|---|---|---|---|---|---|---|---|
| | B*3701 | | B*5801 | | B*5801 | | B*5101 | | Cw*0301 | | Cw*0401 | |
| mAb | none | DX9 | none | DX9 | none | DX9 | none | DX9 | none | DX9 | none | DX9 |
| A. DX9+ NK Clones | | | | | | | | | | | | |
| A4  | +[1] | + | −[2] | + | − | + | − | + | − | − | − | − |
| A6  | +   | + | −   | + | nd | nd | − | + | + | + | nd[3] | nd |
| A7  | +   | + | −   | + | − | + | − | + | − | − | − | − |
| A9  | −   | − | −   | + | − | + | − | + | + | + | − | − |
| A21 | +   | + | −   | + | − | + | − | + | + | + | − | − |
| A23 | +   | + | −   | + | − | + | − | + | − | − | + | + |
| A26 | +   | + | −   | + | − | + | − | + | − | − | − | − |
| A36 | −   | − | −   | + | − | + | − | + | − | − | nd | nd |
| B. DX9− NK Clones | | | | | | | | | | | | |
| B1  | +   | + | −   | − | − | − | + | + | − | − | − | − |
| B2  | −   | − | −   | − | + | + | + | + | + | + | − | − |
| B5  | +   | + | −   | − | − | − | − | − | − | − | − | − |
| B6  | +   | + | −   | − | nd | nd | + | + | + | + | nd | nd |
| B12 | +   | + | −   | − | + | + | + | + | + | + | − | − |
| B19 | +   | + | −   | − | nd | nd | + | + | + | + | nd | nd |

[1]+ Indicates that the % specific lysis of the HLA transfected target cell was comparable to that of the parental cell line or substantially increased in the presence of DX9 mAb. The data are a composite of several experiments.
[2]− Indicates that the % specific lysis of the HLA transfected target cell was 50% or less than that of the parental cell line, i.e.) the NK clone recognizes that particular HLA allele.
[3]Not determined.

This demonstrates that binding DX9 mAb to the NK clones does not interfere with recognition of all HLA molecules, but of only specific alleles. Since some NK clones have the ability to recognize multiple alleles of HLA-B, the effect of DX9 mAb on transfectants expressing B*0702, -B*2705, -B*3701, -B*4801, -B*5101, -B*5401, or -B*5501 was examined. It was consistently observed that DX9 mAb reversed the protection conferred by HLA-B*5101, in addition to HLA-B*5801 (see FIGS. 2A–2D Table 2). HLA-B*5101 and -B*5801 are both within the Bw4 subgroup. DX9 mAb also affected recognition of HLA-B*2705. However, a lower frequency of NK clones recognized HLA-B*2705 compared to HLA-B*5101 and -B*5801 and the protection conferred by -B*2705 was less than with -B*5101 or -B*5801. Consistent with prior observations, NK clones recognizing B*0702, -B*3701, -B*4801, -B*5401, or -B*5501 and the HLA-A alleles (-A*0201, -A*0211, -A*0301, -A*3601, -A*6801) were less frequent than B*5801; however, preliminary studies indicated that DX9 mAb did not consistently or substantially affect lysis of these transfectants. However, a more extensive analysis of NK clones with reactivity with these less frequently protective HLA-A and HLA-B alleles will be required to completely exclude cross-reactivity with these molecules. Similar data were obtained using NKB1+ NK clones derived from two independent donors.

Comparison of NKB1− and NKB1+ NK clones derived from a single donor failed to reveal a strict correlation between the overall pattern of HLA specificity and NKB1 expression (Table 1). Moreover, many NKB1− NK cell clones recognized HLA-B*5801 and -B*5101, although as expected, DX9 mAb failed to affect lysis of these transfectants. Thus, while the results are compatible with the possibility that NKB1 is a receptor for HLA-B*5801 and -B*5101, additional receptors with this specificity apparently are also present on NKB1− NK clones. NKB1− NKclones may express a variant of the molecule not recognized by the mAb or a distinct receptor which also recognizes HLA-B*5801 and -B*5101. There was no apparent bias in the recognition of HLA-A or HLA-C alleles between the clones derived from the NKB1− and NKB1+ NK subsets suggesting the existence of independent receptors for these molecules.

VIII. Structure of NKB1 antigen.

Figure 3A:
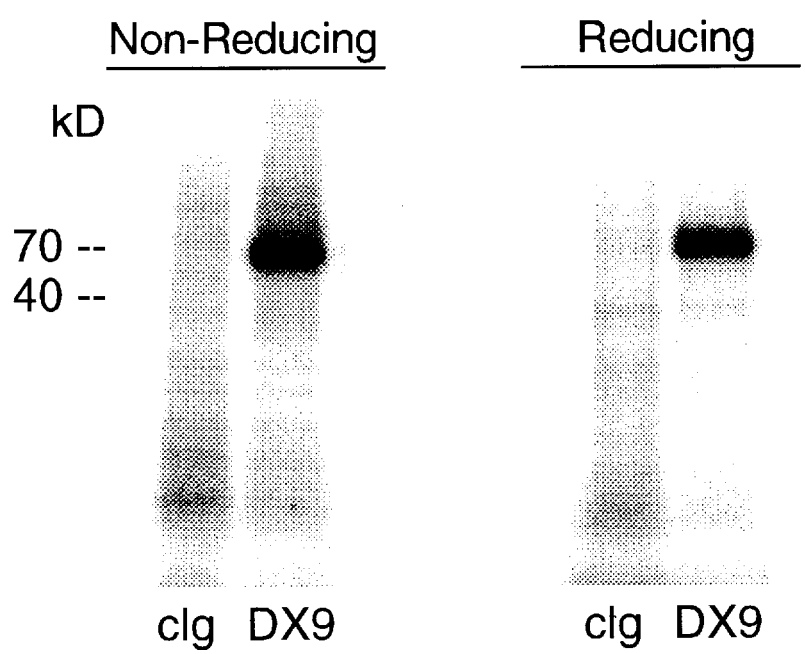
FIGS. 3A–3C shows the structure of NKB1.
Figure 3B:
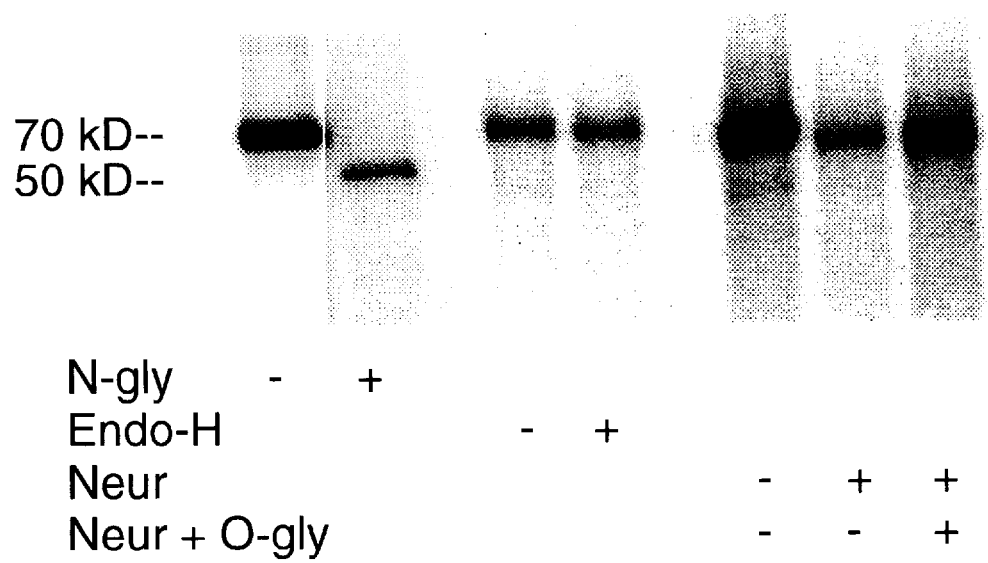
Figure 3C:
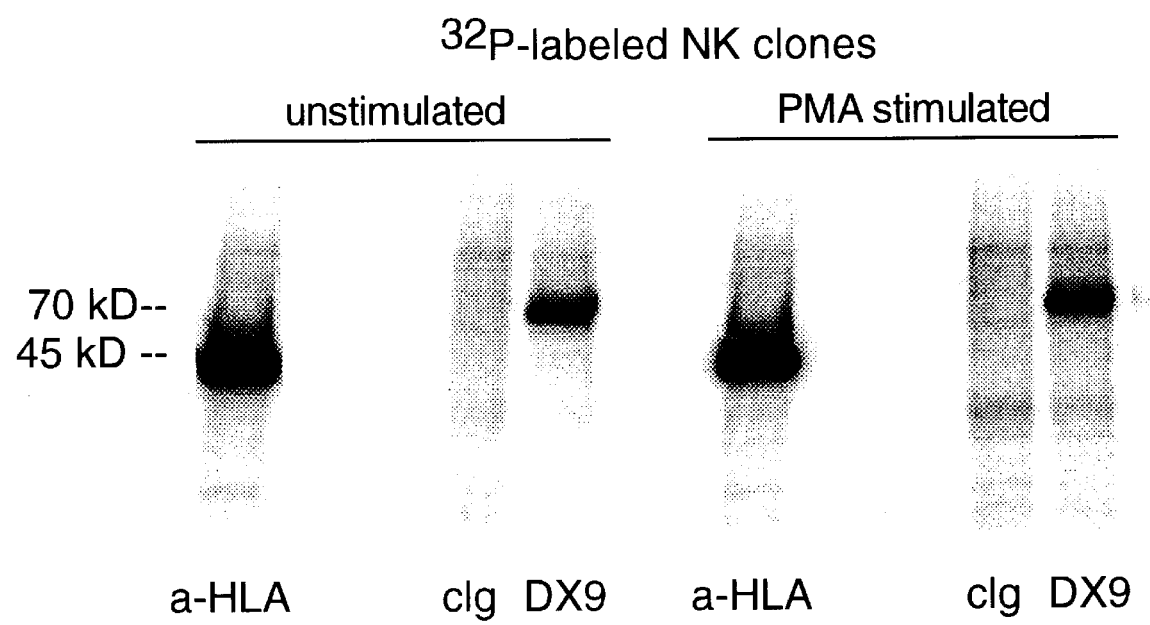

DX9 mAb immunoprecipitated a 70 kD glycoprotein from $^{125}$I labeled NKB1+ NK cell clones that migrated as a single species using both reducing and non-reducing conditions (FIGS. 3A–3C). Identical results were obtained using 1% NP-40 or 1% digitonin detergent for cell disruption. Treatment with neuraminidase slightly decreased the mobility of NKB1, indicating the existence of sialic acid residues. While endo H and O-glycanase failed to affect NKB1, a core protein of ~50 kD was revealed after digestion with N-glycanase, demonstrating the presence of complex N-linked oligosaccharides. Immunoprecipitation from NK cell clones metabolically labeled with $^{32}$p orthophosphate indicated that NKB1 is constitutively phosphorylated. Stimulation with PMA neither increased nor decreased phosphorylation of NKB1.

Conclusions.

Analysis of NK clones using a broad panel of HLA transfectants has shown that multiple receptors for distinct HLA alleles or distinct groups of HLA alleles exist on human NK cells. The present studies show that NKB1 represents one of the NK receptors specific for certain alleles of HLA-B, although formal proof awaits evidence for direct physical binding of purified NKB1 and HLA-B molecules. S&several observations demonstrate that NK cell recognition of HLA is quite complex. First, an individual NK clone apparently can recognize HLA-A, -B, and -C and multiple alleles of each locus. If a sufficiently broad panel of transfectants is examined, recognition of the different alleles can segregate independently in different NK clones. This implies the existence of multiple NK receptors. This is clearly illustrated by comparing NKB1 and NKB1⁺ NK clones. While all NKB1⁺ NK clones examined recognize HLA-B*5801, many NKB1⁻ NK clones were also functionally inhibited by HLA-B*5801, indicating the presence of another HLA-B*5801 receptor on the NKB1⁻ subset. Moreover, NKB1 appears to "cross-react" with HLA-B*5801, -B*5101, and possibly -B*2701.

It is striking that NKB1⁺ NK cells were easily detected in donors which express or lack HLA-B*5801 or HLA-B*5101. The ability to isolate NKB1⁺ NK clones from donors expressing HLA-B*5801 implies that both structures can be present on the same NK cell. Moreover, since NKB1⁺ NK clones from a HLA-B*5801⁺ donor efficiently lysed the HLA-721.221 B-LCL, whereas killing of 721.221 was prevented by transfection with HLA-B*5801, these results indicate that if a "negative signal" is induced it is directional and only functional in the context of the NK cell and target cell interaction. Recent studies using NK cell lines reactive with HLA-C also support the concept that third party cells expressing inhibitory HLA alleles are unable to affect the interaction between an NK cells and a susceptible target.

A further level of complexity is introduced by the expression of NKB1 on only a subset of NK cells and the variable frequency of this subset in different individuals. A similar situation exists with expression of Ly-49 and 5E6 which are expressed only on a subset of NK cells in certain mouse strains. Similarly, the EB6 and GL183 antigens implicated in recognition of HLA-C, also are expressed only on partially overlapping subsets of human NK cells. The biological rationale for multiple HLA receptors distributed on subsets of NK cells is presently unknown.

Prior studies have demonstrated a correlation between expression of EB6 and GL183 and target cell protection by HLA-C. Based on family studies and analysis of HLA-C transfectants, two NK target specificities (designated group 1 and group 2) have been defined based on recognition of certain HLA-C alleles differing at amino acids 77 and 80. NKB1 is clearly distinct both in specificity and structure from the EB6 and GL183 antigens. Certain NKB1⁺ NK clones have the ability to recognize HLA-C alleles of the group 1 or 2 specificities. Both the EB6 /GL183 and NKB1 are structurally different from the murine Ly-49 receptors which are disulfide-linked homodimers. Furthermore, the 70 kD NKB1 glycoprotein is substantially larger than EB6 and GL183 which migrate at 58 kD. Whether these molecules are related awaits direct comparison and cloning of the respective genes. Nonetheless, the data are compatible with the existence of distinct NK receptors for HLA-B and HLA-C on a single NK clone that function independently.

The present invention thus indicates that there are specific antigens important in interaction and/or recognition of specific HLA subtypes of HLA-A, -B, or -C. Herein are provided HLA-B specific reagents, e.g., for HLA-B*5801, and HLA-B*5101. Specific HLA-A and/or HLA-C reagents should also exist.

IX. Isolating a Nucleic Acid Encoding an NKB1.

Numerous methods are available to isolate a gene encoding a purified protein, especially where antibodies which recognize the protein exist. One method is to determine methods for purification of the protein to determine peptide sequences. Given sufficient sequence information, and using redundant oligonucleotides, PCR or hybridization techniques will allow for isolation of genes encoding NKB1 proteins.

Another alternative is to generate additional antibodies to NKB1 proteins. These antibodies are applicable in "panning" techniques, such as described by Seed and Aruffo (1987) *Proc. Nat'l Acad, Sci. USA* 84:3365–3369. Phage expression techniques are also applicable to screen cDNA libraries derived from appropriate NK or T cell subpopulations enriched for NKB1 expression. Glycosylation interference with antibody recognition will be generally less problematic in the phage selection systems. Cell sorting techniques on a mammalian expression library are applicable also.

Another method for screening an expression library is to use antibody to screen successive subpopulations of libraries. The following provides one method of screening using small populations of cells on slides stained by a specific labeling composition, e.g., and antibody.

For example, on day 0, precoat 2-chamber permanox slides with 1 ml per chamber of fibronectin, 10 ng/ml in PBS, for 30 min at room temperature. Rinse once with PBS. Then plate COS cells at 2–3×10⁵ cells per chamber in 1.5 ml of growth media. Incubate overnight at 37° C.

On day 1 for each sample, prepare 0.5 ml of a solution of 66 µg/ml DEAE-dextran, 66 µM chloroquine, and 4 µg DNA in serum free DME. For each set, a positive control is prepared, e.g., of human IL-10-FLAG cDNA construct at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3X with HBSS. The slides may be stored at −80° C. after all liquid is removed. For each chamber, 0.5 ml incubations are performed as follows. Add HBSS/saponin (0.1%) with 32µl/ml of 1M NaN3 for 20 min. Cells are then washed with HBSS/saponin 1X. Soluble antibody, e.g., DX9, is added to cells and incubate for 30 min. Wash cells twice with HBSS/saponin. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85°–90° C.

Alternatively, the NKB1 proteins are used to affinity purify or sort out cells expressing the ligand. See, e.g., Sambrook, et al. or Ausubel, et al., which are incorporated herein by reference.

All references cited herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A binding composition, wherein said composition is an antibody or binding fragment thereof which binds specifically to a natural primate NKB1 characterized by:
   a) specific binding by DX9 (ATCC HB11775);
   b) natural core protein by PAGE of about 50 kD; and
   c) is a recepetor for an HLA-B allele.

2. The binding composition of claim 1, wherein said primate NKB1 is from a human.

3. The binding composition of claim 1, wherein said binding composition:
   a) is sterile;
   b) is immobilized to a solid substrate; or
   c) is detectably labeled.

4. A method of detecting a primate protein, comprising contacting a binding composition of claim 1 to said protein, and detection binding.

5. A method of claim 4, wherein:
   a) said binding composition is a labeled antibody;
   b) said binding composition is immobilized to a solid substrate;
   c) said protein is expressed on a cell surface;
   d) said detecting allows isolation of a cell which comprises a nucleic acid which expresses said protein; or
   e) said detecting further allows purification of said protein.

6. A kit comprising a compartment containing a binding composition of claim 1, and instructions for use in binding to said NKB1.

7. A fluorescence immunoassay kit of claim 6, wherein said binding composition is labeled with a fluorescent marker.

8. The kit of claim 6, wherein said NKB1 exhibits the same molecular weight in reducing and non-reducing conditions.

9. A method for analyzing a sample, comprising measuring the presence of NKB1 with a binding composition of claim 1.

10. The method of claim 9, wherein said measuring is a quantitative determination.

11. The method of claim 9, wherein said measuring is by:
   a) a Fluorescent Activated Cell Sorter (FACS) analysis;
   b) an immunoprecipitation; or
   c) an Enzyme Linked Immuno-Sorbent Assay (ELISA).

12. The method of claim 9, wherein said sample is selected from the group consisting of:
   a) a body fluid;
   b) a cell culture;
   c) a fixed cell;
   d) a live cell; and
   e) a lysate.

13. The binding composition of claim 1, wherein said NKB1:
   a) exhibits a natural PAGE mobility of about 70 kD;
   b) exhibits the same molecular weight in reducing and non-reducing conditions;
   c) decreases PAGE mobility by about 20 kD upon N-glycanase treatment;
   d) exhibits no change in PAGE mobility upon endo-H treatment;
   e) exhibits no change in PAGE mobility upon neuraminidase treatment; or
   f) exhibits no change in PAGE mobility upon treatment with both neuraminidase and O-glycanase.

14. The binding composition of claim 1, which is:
   a) a recombinant protein;
   b) a chimeric antibody; or
   c) a humanized antibody.

15. The binding composition of claim 1, which is:
   a) an F(ab')$_2$ fragment;
   b) an Fab fragment; or
   c) attached to a solid matrix; or
   d) coupled to a toxin or radionuclide.

16. The binding composition of claim 1, which enhances lysis of a cell expressing an HLA-B allele.

17. The binding composition of claim 1, which enhances lysis of a B-LCL cell transformed with an HLA-B allele.

18. A method comprising detecting the presence of a protein on a primate cell population with a binding composition of claim 1.

19. The method of claim 18, wherein said protein exhibits the same PAGE mobility in reducing and non-reducing conditions.

20. The method of claim 18, wherein said binding composition is detectably labeled.

21. The method of claim 18, wherein said population comprises:
   a) $CD3^-CD16^+CD56^+$ NK cells; or
   b) a subset of T cells.

22. The method of claim 18, wherein:
   a) said NKB1 is expressed on a cell surface;
   b) said detecting allows isolation of a cell which comprises a nucleic acid which expresses said protein; or
   c) said detecting further allows purification of said protein.

23. The binding composition of claim 1, which is:
   a) fusion protein with a marker for labeling or detecting; or
   b) conjugated to a drug for targeting.

24. The binding composition of claim 1, characterized by ability to:
   a) interfere with binding of DX9 (HB11775) to said protein; or
   b) enhance lysis of a cell expressing an HLA-B*5801 allele by an NK cell.

25. The binding composition of claim 24, wherein said NKB1:
   a) in its natural form contains sialic acid residues;
   b) in its natural form contains complex N-linked oligosaccharides;
   c) in its natural form is phosphorylated;
   d) is expressed on $CD3^-CD16^+CD56^+$ NK cells; or
   e) is expressed on a subset of T cells.

26. The binding composition of claim 1, wherein said antibody is DX9 (ATCC HB11775).

27. The binding composition of claim 1, wherein said antibody is:
   a) a monoclonal antibody; or
   b) raised to a purified NKB1 antigen.

28. The binding composition of claim 1, which binds to an NKB1 antigen:
   a) in a form exposed to 1% NP-40 or 1% digitonin; or
   b) from a cell lysate.

* * * * *